United States Patent
Matsubara et al.

(10) Patent No.: US 11,396,558 B2
(45) Date of Patent: Jul. 26, 2022

(54) HYPROMELLOSE ACETATE SUCCINATE POWDER EXCELLENT IN DISSOLVED STATE AND PRODUCTION METHOD THEREOF, AND PRODUCTION METHODS FOR COMPOSITION FOR SOLID DISPERSION, COATING COMPOSITION, DRUG-CONTAINING PARTICLE, AND SOLID

(71) Applicant: Shin-Etsu Chemical Co., Ltd., Tokyo (JP)

(72) Inventors: Junichi Matsubara, Joetsu (JP); Naosuke Maruyama, Joetsu (JP); Mitsuhiro Yoshida, Joetsu (JP); Kazuki Kikuchi, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 71 days.

(21) Appl. No.: 17/066,543

(22) Filed: Oct. 9, 2020

(65) Prior Publication Data

US 2021/0024656 A1    Jan. 28, 2021

Related U.S. Application Data

(60) Continuation of application No. 16/789,598, filed on Feb. 13, 2020, now Pat. No. 10,836,836, which is a division of application No. 15/471,224, filed on Mar. 28, 2017, now Pat. No. 10,604,588.

(30) Foreign Application Priority Data

Apr. 5, 2016 (JP) .................. 2016-075801

(51) Int. Cl.
*C08B 13/00* (2006.01)
*A61K 47/38* (2006.01)
*A61K 9/28* (2006.01)
*A61K 9/50* (2006.01)
*A61K 31/525* (2006.01)

(52) U.S. Cl.
CPC ............ *C08B 13/00* (2013.01); *A61K 9/2866* (2013.01); *A61K 9/5042* (2013.01); *A61K 9/5089* (2013.01); *A61K 31/525* (2013.01); *A61K 47/38* (2013.01)

(58) Field of Classification Search
CPC .... C08B 13/00; A61K 9/2866; A61K 9/5042; A61K 9/5089; A61K 31/525; A61K 47/38
See application file for complete search history.

(56) References Cited

FOREIGN PATENT DOCUMENTS

| CA | 2934231 | 7/2015 |
| EP | 2837391 | 2/2015 |
| JP | 07109219 | 4/1995 |
| JP | 08245423 | 9/1996 |

OTHER PUBLICATIONS

D. T. Friesen, R. Shanker, / M. Crew, D. T. Smithey, W. J. Curatolo, and J. A. S. Nightingale. "Hydroxypropyl Methylcellulose Acetate Succinate-Based Spray-Dried Dispersions: An Overview," Molecular Pharmaceutics, 2018, vol. 5, No. 6, 1003-1019. (Year: 2008).*
Google_scholar_search_2-23-22_hypromellose_acetate_succinate_coatings (Year: 2022).*
Google_scholar_search_2-23-22_hypromellose_acetate_succinate_particle_size (Year: 2022).*
Extended European Search Report corresponding to European Patent Application No. 17164369.5 (9 pages) (dated Aug. 14, 2017).
Friesen et al. "Hydroxypropyl Methylcellulose Acetate Succinate-Based Spray-Dried Dispersions: An Overview" Molecular Pharmaceutics, 5(6)1003-1019(2008).
Mukai et al. "The Dust Explosibility of Several Kinds of Cellulose Derivatives" Funtai Kogaku Kaishi Journal, 32(1):4-9 (1995) (English translation of abstract).
Rowe et al. "Hypromellose Acetate Succinate" Handbook of Pharmaceutical Excipients 5th Edition, pp. 350-353 (2006).
Sarode et al. "Stability assessment of hypromellose acetate succinate (HPMCAS) NF for application in hot melt extrusion (HME)" Carbohydrate Polymers 101:146-153 (2014).
"Shin-Etsu AQOAT" Product description, downloaded Jun. 19, 2018 from http://www.elementoorganika.ru/files/aqoat; dated Oct. 2005 (20 pages).
"Solubility of Things—definition of Soluble", downloaded Jun. 20, 2018 from http://wwww.solubilityofthings.com/soluble-compounds-definition-level-solubility (Year:2018) (1 page).
Zimmerman, Ingfried "Direkt abbildende optische Messverfahren" Pharmazeutische Technologie pp. 246-247 (1998) (concise statement).

* cited by examiner

Primary Examiner — Michael P Cohen
(74) Attorney, Agent, or Firm — Myers Bigel, P.A.

(57) ABSTRACT

Provided are HPMCAS powder having high solubility when dissolved in a solvent and being capable of suppressing generation of undissolved materials; and a method for producing the powder. More specifically, provided is hypromellose acetate succinate powder having an average ratio of L to D of from 2.0 to 3.0, wherein L and D mean maximum and minimum diameters of each particle, respectively. Also provided is a method for producing a hypromellose acetate succinate, comprising the steps of: dissolving hypromellose powder in a solvent, esterifying the dissolved hypromellose with succinic anhydride and acetic anhydride in the presence of a catalyst to obtain a reaction mixture, and mixing the reaction mixture with water to precipitate hypromellose acetate succinate, wherein the reaction mixture just before being mixed with the water has a viscosity of from 100 to 200 Pa·s.

7 Claims, No Drawings

HYPROMELLOSE ACETATE SUCCINATE POWDER EXCELLENT IN DISSOLVED STATE AND PRODUCTION METHOD THEREOF, AND PRODUCTION METHODS FOR COMPOSITION FOR SOLID DISPERSION, COATING COMPOSITION, DRUG-CONTAINING PARTICLE, AND SOLID

RELATED APPLICATIONS

This application is a continuation of U.S. patent application Ser. No. 16/789,598, filed Feb. 13, 2020, which is a divisional of U.S. patent application Ser. No. 15/471,224, filed Mar. 28, 2017, which claims priority from Japanese Patent Application No. 2016-075801, filed Apr. 5, 2016, the disclosures of each of which are incorporated by reference herein in their entirety.

FIELD OF THE INVENTION

The present invention relates to hypromellose acetate succinate powder excellent in solubility and pharmaceutical use thereof.

BACKGROUND

Hypromellose acetate succinate is a widely known enteric polymer. It is a polymer obtained by introducing four kinds, in total, of substituents to the cellulose backbone. More specifically, the hypromellose acetate succinate has ether structures formed by introduction of two substituents, a methyl group (-CH$_3$) and a hydroxypropyl group (—C$_3$H$_6$OH), and ester structures formed by introduction of two substituents, an acetyl group (—COCH$_3$) and a succinyl group (—COC$_2$H$_4$COOH).

The hypromellose acetate succinate (hereinafter also referred to as "HPMCAS"), which is an enteric polymer, has been widely used for a solid dispersion for improving the dissolution properties of a poorly water-soluble drug, and for enteric coating.

The solid dispersion is obtained, for example, by solidification through hot melt extrusion of a poorly water-soluble drug and the polymer. Alternatively, attention is now paid to a method such as spray-drying. The spray-drying for producing a solid dispersion comprises the steps of: dissolving a mixture of a drug and the polymer in a solvent and then removing the solvent for deposition. For example, a solid dispersion obtained by spray-drying a solution of a poorly water-soluble drug and the polymer has improved bioavailability because the drug is molecularly dispersed in amorphous form in a polymer carrier to markedly and seemingly increase a solubility.

An enteric coating preparation is one of important preparations widely used for administration of an acid-labile drug or for protection of the gastric mucosa. In conventional production of an enteric coating preparation, it is the common practice to use a method comprising the steps of: dissolving an enteric polymer in an organic solvent, and spraying the resulting solution to form an enteric film on the surface of a drug. A so-called aqueous enteric coating method using an aqueous dispersion of a finely pulverized enteric polymer has been developed in consideration of environmental conservation or safety against use of an organic solvent (JP 07-109219A). For example, there is reported an ammonia-neutralized coating method using an aqueous enteric coating solution obtained by dissolving HPMCAS, which is an enteric polymer, in such an amount of ammonia as to be required for neutralizing about 80 mol % or more of the carboxyl group in the molecule of the HPMCAS (JP 08-245423A).

SUMMARY OF THE INVENTION

It is the common practice to remove undissolved materials from a composition having HPMCAS alone dissolved therein or having both a drug and HPMCAS dissolved therein through a filter before coating or spray-drying. However, a large amount of the undissolved materials may deteriorate workability due to clogging of the filter with the undissolved materials. Even if a filter is not used, there is a possibility of causing clogging of a nozzle during coating or spray drying.

In addition, the aqueous enteric coating composition is sensitive to heat so that the enteric polymer may be aggregated to make a spray nozzle clogged with the enteric polymer during coating, requiring a high-level technology for forming a film from the aqueous dispersion. Further, the ammonia-neutralized coating method requires long hours for dissolving HPMCAS. Even if the dissolution time is prolonged, the HPMCAS cannot be dissolved completely and undissolved materials remain. A coating composition containing such undissolved materials therein cannot provide intended acid resistance because a nozzle is clogged during coating or a film thus obtained lacks uniformity.

Accordingly, conventional HPMCAS is required to have further improved solubility.

With the foregoing in view, the invention has been made. An object of the invention is to provide HPMCAS powder exhibiting excellent solubility when dissolved in a solvent and capable of suppressing generation of undissolved materials, and a method for producing the powder. Another object is to provide a method for producing a composition for solid dispersion, the composition containing the HPMCAS powder; a method for producing a coating composition containing the HPMCAS powder; a method for producing a drug-containing particle; and a method for producing the solid preparation; where each method can be carried out in a short period of time.

As a result of an extensive investigation with a view to achieving the above-described objects, the inventors have paid attention to the shape of HPMCAS powder. Finding that HPMCAS powder having an average ratio of L to D (i.e. L/D) adjusted to fall within a predetermined range can have improved solubility in a solvent, wherein L and D means maximum and minimum diameters of each particle, respectively, the inventors have completed the invention. More specifically, the inventors have found that contrary to an expectation that the smaller the ratio of L/D becomes, the higher dispersibility and solubility become, the solubility can be improved by increasing the ratio of L/D. The solvent to be used is, for example, acetone, a mixed solution of water and an alcohol, or an aqueous ammonia solution. Generation of undissolved materials can be suppressed because HPMCAS powder having a specific L/D ratio are excellent in solubility.

In one aspect of the invention, there is provided hypromellose acetate succinate powder having an average ratio of L to D (i.e. L/D) of 2.0 to 3.0, wherein L and D mean maximum and minimum diameters of each particle, respectively. In another aspect of the invention, there is provided a method for producing a composition for solid dispersion, comprising the step of removing a solvent from a solution comprising the hypromellose acetate succinate powder, a drug, and the solvent. In a still another aspect of the invention, there is provided a method for producing a coating composition, comprising the step of dissolving the hypromellose acetate succinate powder in a solvent which is a mixed solution of water and an alcohol, or an aqueous ammonia solution. In a further aspect of the invention, there are provided a method for producing a drug-containing particle, comprising: each step comprised by the method for producing the coating composition and a step of coating a drug-containing core with the coating composition to form a coat portion over the core; and a method for producing a solid preparation, comprising: the steps comprised by the method for producing the drug-containing particle and a step of formulating the drug-containing particle into a preparation. In a still further aspect, there is also provided a method for producing hypromellose acetate succinate powder, comprising the steps of: dissolving hypromellose in a solvent, esterifying the dissolved hypromellose with succinic anhydride and acetic anhydride in the presence of a catalyst to obtain a reaction mixture, and mixing the reaction mixture with water to precipitate hypromellose acetate succinate, wherein the reaction mixture just before being mixed with the water has a viscosity of from 100 to 200 Pa·s.

According to the invention, the HPMCAS powder can have improved solubility when dissolved in a solvent. For example, the HPMCAS powder has improved solubility when dissolved in a solvent which is a mixed solution of water and an alcohol, or an aqueous ammonia solution. This makes it possible to prepare a coating solution in a short time and suppress generation of undissolved materials. In addition, when the undissolved materials is filtered out from the liquid composition containing the HPMCAS powder dissolved therein, clogging of the filter can be reduced.

DETAILED DESCRIPTION OF THE EXAMPLE EMBODIMENTS (1) HPMCAS Powder

The average ratio of L/D of the HPMCAS powder, wherein L means a maximum diameter and D means a minimum diameter of each particle, is from 2.0 to 3.0, preferably from 2.2 to 2.8, more preferably from 2.4 to 2.6. When the average L/D ratio is less than 2.0, an amount of an undissolved residue in acetone mainly used as a solvent for a composition for solid dispersion becomes large relative to the amount of the HPMCAS dissolved in the solvent. In addition, the HPMCAS powder having the average L/D ratio of less than 2.0 exhibits low solubility in an aqueous ammonia solution used for preparation of a coating composition so that it takes time to prepare the composition and the amount of undissolved materials increases. When the average L/D ratio is more than 3.0, although the solubility is improved, workability is lowered because an increase in the viscosity of the reaction mixture reduces flowability of the powder, making it difficult to transfer the reaction mixture to the subsequent step.

It has been considered from the standpoint of dispersibility of the HPMCAS powder in a solvent to have improved solubility that the smaller the L/D ratio becomes, the better dispersibility and solubility in the solvent become, wherein L and D mean maximum and minimum diameters of each particle, respectively. On the other hand, it has been considered that the larger the L/D ratio becomes, the more inferior the solubility becomes, because an amount of undissolved lumps increases. However, with respect to the actual solubility of the HPMCAS powder, contrary to the above expectation, the powder having a larger L/D ratio exhibit improved solvent penetration and therefore have improved solubility.

The average L/D ratio of the HPMCAS powder can be determined in the method comprising the steps of: dispersing 1 mg of the HPMCAS powder in a ϕ90×15 petri dish, measuring the maximum diameter (L) and the minimum diameter (D) of each particle at 50× magnification using a digital microscope "VHX-2000" (product of KEYENCE) to obtain an L/D ratio of each particle, wherein the number of the particles measured by one measurement is 30 or more and such a measurement is performed 10 times or more so that an average of 300 or more particles in total is determined to obtain the average L/D ratio of the powder.

The specific surface area of the HPMCAS powder is preferably from 2.0 to 5.0 $m^2/g$, more preferably from 3.0 to 5.0 $m^2/g$, still more preferably from 3.5 to 5.0 $m^2/g$ from the standpoint of solubility and flowability. The specific surface area is measured by a method of determining the specific surface area of a sample from the adsorption amount, where the surfaces of the sample powder particles adsorb each molecule having a known adsorption occupied area at a temperature of liquid nitrogen (−196° C.). The BET method (BET multipoint measurement) using low-temperature low humidity physical adsorption of an inert gas can be used. For example, it can be measured in accordance with "Method 2: The volumetric method" of "Specific Surface Area by Gas Adsorption" in General Tests of the Japanese Pharmacopoeia Sixteenth Edition. An automated specific surface area and pore distribution analyzer TriStar II 3020 (product of Micromeritics) can be used for the measurement.

The HPMCAS powder has a loose bulk density of preferably from 0.10 to 0.25 g/mL, more preferably from 0.10 to 0.20 g/mL, still more preferably from 0.10 to 0.15 g/mL from the standpoint of solubility and flowability. The term "loose bulk density" means a bulk density in a loosely filled state. The loose bulk density can be determined by the method comprising the steps of: uniformly feeding a sample which has passed through a HS 22-mesh sieve (openings: 710 μm), into a stainless steel cylindrical vessel having a diameter of 5.03 cm and a height of 5.03 cm (volume: 100 ml) from 23 cm above a top surface of the vessel; and leveling off the top surface of the sample for weighting.

According to the invention, the HPMCAS powder can have improved solubility when dissolved in a solvent. For example, a portion of a component of the hypromellose acetate succinate powder, the component being not soluble at 20° C. in such a weight of acetone as to be 10 times the weight of the powder, is preferably 10% by weight or less. In other words, this proportion means an undissolved residue proportion when the hypromellose acetate succinate ester powder is dissolved at 20° C. in such a weight of acetone as to be 10 times the weight of the powder. In addition, according to the invention, the HPMCAS powder can have improved solubility in a solvent which is, for example, a mixed solution of water and an alcohol, or an aqueous ammonia solution.

(2) Production Method of HPMCAS Powder

The method for producing the HPMCAS powder comprises a dissolution step of dissolving hypromellose in a solvent, an esterification step of reacting the dissolved hypromellose with an esterifying agent in the presence of a catalyst to obtain a reaction mixture, and a precipitation step of mixing the reaction mixture with water to precipitate hypromellose acetate succinate. The reaction mixture before being mixed with water has a viscosity of preferably from 100 to 200 Pa·s.

Hypromellose (another name: hydroxypropyl methyl cellulose; hereinafter also referred to as "HPMC") to be used as a raw material can be obtained by a known method, for example, a method comprising the steps of: bringing pulp in form of sheet, chips, or powder into contact with an alkali such as sodium hydroxide or potassium hydroxide to obtain alkali cellulose and reacting the alkali cellulose with an etherifying agent such as methyl chloride or propylene oxide.

The alkali metal hydroxide solution to be used is not particularly limited insofar as it can provide alkali cellulose. The alkali metal hydroxide solution is preferably an aqueous solution of sodium hydroxide or potassium hydroxide from the standpoint of economy. The concentration of the alkali metal hydroxide solution is preferably from 23 to 60% by weight, more preferably from 35 to 55% by weight from the standpoint of the stable composition of the alkali cellulose and transparency of the cellulose ether.

After the alkali cellulose is produced, an etherifying agent such as methyl chloride or propylene oxide is added thereto for an etherification reaction to obtain HPMC in a conventional manner.

The HPMC thus obtained has a degree of substitution (DS) of methoxy groups of preferably from 0.73 to 2.83 (from 28.0 to 30.0% by weight), more preferably from 1.25 to 2.37 (from 28.8 to 29.2% by weight), and a molar substitution (MS) of hydroxypropoxy groups of preferably from 0.10 to 1.90 (from 8.5 to 10.0% by weight), more preferably from 0.12 to 0.95 (from 8.8 to 9.2%). The degree of substitution of methoxy groups and the molar substitution of hydroxypropoxy groups can be obtained, for example, from the calculation using the values obtained by an analysis method specified in "Hypromellose" of the Japanese Pharmacopoeia Sixteenth Edition.

The viscosity at 20° C. of a 2% by weight aqueous HPMC solution is determined in accordance with viscosity measurement by the capillary tube viscometer in the Japanese Pharmacopoeia Sixteenth Edition, and is preferably from 2.2 to 7.2 mPa·s, more preferably from 3.0 to 3.5 mPa·s.

HPMCAS powder can be produced using the HPMC thus obtained and by the method comprising a dissolution step, an esterification step, a precipitation step, and a washing and drying step.

In the dissolution step, the HPMC is dissolved in a solvent such as glacial acetic acid. The solvent may be used in an amount of preferably from 1.0 to 3.0 times, more preferably from 1.2 to 2.5 times, still more preferably from 1.5 to 2.0 times, particularly preferably from 1.5 to 1.8 times the weight of the HPMC from the standpoint of a reaction rate.

In the esterification step, the HPMC in the resulting solution is reacted with succinic anhydride and acetic anhydride in the presence of a catalyst to obtain a reaction mixture.

The amount of succinic anhydride to be used is preferably from 0.1 to 1.0 mol, more preferably from 0.1 to 0.8 mol, still more preferably from 0.3 to 0.5 mol relative to 1 mol of the raw material HPMC from the standpoint of a composition and a yield. The amount of acetic anhydride to be used is preferably from 0.2 to 1.5 mol, more preferably from 0.4 to 1.3 mol, still more preferably from 1.1 to 1.3 mol relative to 1 mol of the raw material HPMC from the standpoint of a composition and a yield.

A molar substitution (MS) of succinyl groups of the HPMCAS is preferably from 0.10 to 2.50, more preferably from 0.10 to 1.00, still more preferably 0.10 to 0.60. A degree of substitution (DS) of acetyl groups of the HPMCAS is preferably from 0.10 to 2.50, more preferably from 0.10 to 1.00, still more preferably from 0.40 to 0.96. The molar substitution of succinyl groups and the degree of substitution of acetyl groups can be obtained, for example, from the calculation using the values obtained by an analysis method specified in "Hypromellose" of the Japanese Pharmacopoeia Sixteenth Edition.

The catalyst to be used in the esterification step is preferably an alkali metal carboxylate such as sodium acetate from standpoint of economy. The amount of the catalyst to be used is preferably from 0.8 to 1.5 mol, more preferably from 0.9 to 1.1 mol relative to 1 mol of the raw material HPMC from the standpoint of a composition and a yield.

In the esterification reaction, a biaxial stirrer suited for forming a uniform mixture from a highly viscous fluid and kneading the resulting mixture may be used. Generally, it is commercially available under the name of a kneader, an internal mixer or the like.

The reaction temperature in the esterification step is preferably from 60 to 100° C., more preferably from 80 to 90° C. from the standpoint of a reaction rate or a viscosity increase. The reaction time in the esterification step is preferably from 2 to 8 hours, more preferably from 3 to 6 hours.

After the esterification reaction, water can be added to the reaction mixture to treat an unreacted portion of the succinic anhydride and acetic anhydride and to control the viscosity of the reaction mixture. An amount of water to be added is preferably from 0.8 to 1.5 times, more preferably from 1.0 to 1.3 times the weight of the HPMC. When the amount of water is less than 0.8 times the weight of the HPMC, the reaction mixture may have an increased viscosity. When the amount of water is more than 1.5 times, the transfer of the reaction mixture may become difficult due to precipitation of the HPMCAS.

The viscosity of the reaction mixture obtained by the esterification reaction can be measured using, for example, a model TVC-7 viscometer (Brookfield B-type rotational viscometer) of TOKI SANGYO CO., LTD. In order to make an average L/D ratio of the HPMCAS powder become 2.0 to 3.0, wherein L and D mean maximum and minimum diameters of each particle, the viscosity of the reaction mixture just before being mixed with water in the precipitation step is adjusted to preferably from 100 to 200 Pa·s, more preferably from 120 to 190 Pa·s, still more preferably from 140 to 190 Pa·s. Although the reason is not known, "the viscosity of the reaction mixture just before contact with water" is important. On the other hand, for example, "the viscosity of the reaction mixture after contact with water" including the viscosity of the reaction mixture just after the contact with water, a contact rate with the water, and a temperature lowering rate of the reaction mixture do not have to be considered.

The temperature of the reaction mixture just before being mixed with the water in the precipitation step is preferably from 10 to 30° C., more preferably from 10 to 20° C., still more preferably from 15 to 20° C. In order to adjust the "temperature of the reaction mixture just before contact with water" to be in the above range, the reaction mixture may be cooled with a jacket of a reaction stirrer.

In the precipitation step, the reaction mixture thus obtained is mixed with water to obtain hypromellose acetate succinate. The amount of water is preferably from 2.5 to 7.0 times, more preferably from 3.0 to 5.0 times the weight of the reaction mixture from the standpoint of a degree of precipitation and treatment time. The temperature of water to be mixed is preferably from 5 to 40° C.

In the washing and drying step, the HPMCAS thus precipitated is washed sufficiently with water to wash out free acetic acid and free succinic acid, and then dried at preferably from 60 to 100° C., more preferably from 70 to 80° C., for preferably from 1 to 5 hours, more preferably from 2 to 3 hours. As a result, a high-purity product can be obtained.

(3) Composition for Solid Dispersion

The composition for solid dispersion comprises the HPMCAS powder having an average L/D ratio of from 2.0 to 3.0, a drug and a solvent, wherein L and D means maximum and minimum diameters of each particle.

Examples of the solvent to be used for the composition for solid dispersion include acetone, methanol, ethanol, isopropanol, methyl acetate, ethyl acetate, tetrahydrofuran, dichloromethane, and mixtures thereof. The solvent is preferably acetone particularly from the standpoint of solubility.

Examples of the drug to be used for the composition for solid dispersion include a poorly soluble drug having low solubility in water, where 1000 mL or more water is necessary for dissolving 1 g of the drug. Examples of the drug include azole-based compounds such as itraconazole, ketoconazole, fluconazole and mitoconazole; dihydropyridine-based compounds such as nifedipine, nitrendipine, amlodipine, nicardipine, nilvadipine, felodipine and efonidipine; propionic acid-based compounds such as ibuprofen, ketoprofen and naproxen; and indoleacetic acid-based compounds such as indomethacin and acemetacin. Additional examples include griseofulvin, phenytoin, carbamazepine and dipyridamole.

The solid dispersion can be produced by the method comprising the steps of: preparing a solution comprising the HPMCAS powder, a drug and an optional component such as an excipient, a binder, a disintegrant, a lubricant or an aggregation preventive, and removing the solvent from the solution. The composition for solid dispersion may be provided in any of a suspension, a uniform solution, or a combination of dissolved and suspended substances. The uniform solution having HPMCAS and a drug uniformly dissolved is preferred.

Examples of the method of removing the solvent include distilling to dryness and spray-drying. The term "spray-drying" widely means a method for breaking (spraying) a solution mixture containing a poorly water-soluble drug into small droplets and rapidly removing the solvent from the droplets by evaporation. Preferred embodiments of the spray-drying include a method of mixing the droplets with a high-temperature drying gas and a method of maintaining the pressure in the solvent-removal apparatus at incomplete vacuum.

(4) Coating Composition

The coating composition comprises the HPMCAS powder having an average L/D ratio of from 2.0 to 3.0, and a solvent which is a mixed solution of water and an alcohol, or an aqueous ammonia solution. The L and D mean maximum and minimum diameters of each particle. The concentration of the HPMCAS powder in the coating composition is preferably from 5 to 20% by weight, more preferably from 7 to 15% by weight from the standpoint of the solution viscosity and productivity.

Examples of the solvent for the coating composition include a mixed solution of water and an alcohol such as methanol, ethanol or isopropanol, having a weight ratio of the water to the alcohol of (from 2 to 4):(from 6 to 8), in other words, from (1:1.5) to (1:4), and an aqueous ammonia solution having an ammonia concentration of 0.01 to 1.0% by weight.

The method for producing the coating composition preferably comprises a step of dissolving the HPMCAS powder in the solvent which is a mixed solution of water and an alcohol, or an aqueous ammonia solution. When the aqueous ammonia solution is used as the solvent, the HPMCAS powder is dispersed in water of normal temperature, and then mixed, while stirring, with the aqueous ammonia solution having an ammonia concentration of, for example, from 5 to 30% by weight, in an amount necessary for neutralizing the carboxyl group of the HPMCAS until the HPMCAS is dissolved. In this step, ammonia is used preferably in an equimolar amount (i.e. 100%) to the carboxyl group, more preferably 80% or more of the equimolar amount, still more preferably from 95 to 105% of the equimolar amount, from the standpoint of solubility of the HPMCAS and acid resistance of a solid preparation having the coating composition applied thereto.

The coating composition may comprise an optional various additive conventionally used in this field, such as a lubricant, another coating base, a plasticizer, a surfactant, a colorant, a pigment, a sweetener and an antifoaming agent, in a conventional amount.

Examples of the lubricant include talc, magnesium stearate, calcium stearate, colloidal silica and stearic acid. The amount of the lubricant is not particularly limited insofar as it does not hinder the advantage of the invention. The lubricant is added in an amount of preferably 200 parts by weight or less, more preferably 100 parts by weight or less relative to 100 parts by weight of the HPMCAS powder. The talc is particularly preferred for preventing the particles from adhering to each other during coating.

Another coating base is a coating base other than HPMCAS which is an enteric base. Examples of another coating base include a water-soluble vinyl derivative such as polyvinylpyrrolidone and polyvinyl alcohol; a water-insoluble cellulose ether such as ethyl cellulose; and an acrylic acid type copolymer such as methacrylic acid copolymer LD and an ethyl acrylate-methyl methacrylate copolymer dispersion. An amount of another coating base is not particularly limited insofar as it does not hinder the advantage of the invention. It is preferably not more than 100 parts by weight, more preferably not more than 50 parts by weight, relative to 100 parts by weight of the HPMCAS powder.

Examples of the plasticizer include citrates such as triethyl citrate and acetylated triethyl citrate; polyethylene glycol; propylene glycol; glycerin; glycerin fatty acid esters such as triacetin and monoacetyl glycerin; and dibutyl phthalate. An amount of the plasticizer is not particularly limited insofar as it does not hinder the advantage of the invention. It is preferably not more than 100 parts by weight, more preferably not more than 50 parts by weight, relative to 100 parts by weight of the HPMCAS powder.

(5) Drug-Containing Particle

The drug-containing particle comprises a drug-containing core and a coat portion obtained by coating of the above-described coating composition.

The method for producing the drug-containing particle preferably comprises the step of producing the coating composition and a step of coating a drug-containing core with the coating composition to form a coat portion over the core. For example, the drug-containing particle can be produced by coating a drug-containing core with the coating composition by using a conventionally known coater. The coater is not particularly limited. Examples of the coater include a pan coater, a fluidized-bed coater and a tumbling fluidized bed coater. Examples of the coating method include a method of applying the prepared coating composition to the drug-containing core.

The drug to be used for the drug-containing core is a conventionally used drug and is not particularly limited insofar as it is orally administrable. Examples of the drug include a central nervous system drug, a circulatory system drug, a respiratory system drug, a digestive system drug, an antibiotic, an antitussive and expectorant drug, an antihistamine drug, an antipyretic, analgesic and anti-inflammatory drug, a diuretic drug, an autonomic drug, an antimalarial drug, an anti-diarrheal drug, a psychotropic drug, and vitamins and derivatives thereof.

Examples of the central nervous system drug include diazepam, idebenone, paracetamol, naproxen, piroxicam, indomethacin, sulindac, lorazepam, nitrazepam, phenytoin, acetaminophen, ethenzamide, and chlordiazepoxide.

Examples of the circulatory system drug include molsidomine, vinpocetine, propranolol, methyldopa, dipyridamole, furosemide, triamterene, nifedipine, atenolol, spironolactone, metoprolol, pindolol, captopril, isosorbide nitrate, delapril hydrochloride, meclofenoxate hydrochloride, diltiazem hydrochloride, etilefrine hydrochloride, digitoxin, and alprenolol hydrochloride.

Examples of the respiratory system drug include amlexanox, dextromethorphan, theophylline, pseudoephedrine, salbutamol, and guaifenesin.

Examples of the digestive system drug include a benzimidazole-based drug having an anti-ulcer action such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicyclic acid.

Examples of the antibiotic include talampicillin hydrochloride, bacampicillin hydrochloride, cefaclor, and erythromycin.

Examples of the antitussive and expectorant drug include noscapine hydrochloride, carbetapentane citrate, isoaminile citrate, and dimemorfan phosphate.

Examples of the antihistamine drug include chlorpheniramine maleate, diphenhydramine hydrochloride, and promethazine hydrochloride.

Examples of the antipyretic, analgesic and anti-inflammatory drug include ibuprofen, diclofenac sodium, flufenamic acid, sulpyrine, aspirin, and ketoprofen.

Examples of the diuretic drug include caffeine.

Examples of the autonomic drug include dihydrocodeine phosphate, dl-methylephedrine hydrochloride, atropine sulfate, acetylcholine chloride, and neostigmine.

Examples of the antimalarial drug include quinine hydrochloride.

Examples of the anti-diarrheal drug include loperamide hydrochloride.

Examples of the psychotropic drug include chlorpromazine.

Examples of the vitamins and derivatives thereof include Vitamin A, Vitamin B1, fursultiamine, Vitamin B2, Vitamin B6, Vitamin B12, Vitamin C, Vitamin D, Vitamin E, Vitamin K, calcium pantothenate, and tranexamic acid.

Examples of the drug-containing core may include an active ingredient of a drug; a granule obtained by wet granulation, dry granulation or the like; and a layered particle obtained by coating (layering) the periphery of a core such as crystalline cellulose, mannitol or lactose with the drug. During the production of the drug-containing core by granulation or layering, a various additive conventionally usable in this field, such as an excipient, a binder or a disintegrant, may be incorporated.

The amount of the coating composition to be used for coating the surface of the drug-containing core differs depending on the shape or size of the drug-containing core, or properties of the drug or additive contained by the core. Roughly speaking, the coating amount of the HPMCAS is preferably from 1 to 500 parts by weight, more preferably from 5 to 100 parts by weight, still more preferably from 10 to 50 parts by weight relative to 100 parts by weight of the drug-containing core. When the coating amount of the HPMCAS is smaller than the above-described range, an uncomfortable taste may not be suppressed sufficiently. When the coating amount of the HPMCAS is larger than the above-described range, it takes long hours to finish the production so that it may not be practical.

The coat portion is not limited insofar as it contains the coating composition. The coat portion (coating layer) may be composed only of the coating composition, or may comprise the coat of the coating composition and the undercoat containing another coating base under the coat of the coating composition. As another coating base, a various coating base conventionally usable in this field, such as hydroxypropyl methyl cellulose, can be used. The coat portion may be in any form such as layer form or film form without particular limitation.

The drug-containing particle comprising the core and the coating composition has an average particle size of preferably 300 μm or less, more preferably 250 μm or less so as to prevent uncomfortable rough feel in the oral cavity.

The average particle size is a volume-based particle size and is determined by powder particle size measurement using laser diffraction. For example, HELOS & RODOS (product of Japan Laser Corporation) can be used for the measurement.

One or more films or layers may be formed between the drug-containing core and the coat layer made of the coating composition, by adding a step of undercoating the core with a various coating base conventionally usable in this field such as hypromellose.

(6) Solid Preparation Containing Drug-Containing Particle

Examples of the solid preparation include a tablet, a granule, a fine granule, and a capsule. The Examples also include an orally disintegrating tablet. The solid preparation may comprise, as well as the drug-containing particle, a various additive usable conventionally in this field such as an excipient, a binder, a disintegrant, a lubricant, an anti-aggregation agent, or a solubilizing agent of a pharmaceutical compound.

Examples of the excipient include a saccharide such as sucrose, lactose and glucose; a sugar alcohol such as mannitol, sorbitol and erythritol; starch; crystalline cellulose; calcium phosphate; and calcium sulfate.

Examples of the binder include polyvinyl alcohol, polyacrylic acid, polymethacrylic acid, polyvinylpyrrolidone, glucose, sucrose, lactose, maltose, dextrin, sorbitol, mannitol, hydroxyethyl cellulose, hydroxypropyl methyl cellulose, hydroxypropyl cellulose, macrogols, gum arabic, gelatin, agar and starch.

Examples of the disintegrant include low-substituted hydroxypropyl cellulose, carmellose or salt thereof, croscarmellose sodium, carboxymethyl starch sodium, crospovidone (another name: polyvinylpyrrolidone), crystalline cellulose, and a combination of crystalline cellulose and carmellose sodium.

Examples of the lubricant and the anti-aggregation agent include talc, magnesium stearate, calcium stearate, colloidal silica, stearic acid, waxes, hydrogenated oils, polyethylene glycols, and sodium benzoate.

Examples of the solubilizing agent of a pharmaceutical compound include an organic acid such as fumaric acid, succinic acid, malic acid and adipic acid.

The method for producing a solid preparation comprises each step comprised by the method for producing a drug-containing particle and a step of formulating the drug-containing particle into a preparation. Examples of the step of formulating include a step of tableting the drug-containing particle into a tablet, and a step of granulating the drug-containing particle into a granule or a fine granule.

EXAMPLES

The invention will hereinafter be described specifically by Synthesis Examples and Examples. It should not be construed that the invention is limited to or by Synthesis Examples and Examples.

Synthesis Example 1

Hydroxypropyl methyl cellulose (HPMC) had a molar substitution (MS) of hydroxypropoxy groups of 0.24 per glucose unit and a degree of substitution (DS) of methoxy groups of 1.89 per glucose unit, and a viscosity at 20° C. of a 2% by weight aqueous solution of the HPMC was 3.34 mPa·s. The 600 g of the HPMC was dissolved in glacial acetic acid and reacted with succinic anhydride and acetic anhydride in the presence of sodium acetate at 85° C. for 5 hours. The respective amounts of the glacial acetic acid, succinic anhydride and acetic anhydride are shown in Table 1.

Next, the reaction mixture was subjected to addition of such an amount of water as to make the viscosity of the reaction mixture become 150 Pa·s, and then subjected to gradual addition of water of 25° C. in an amount of 4 times the weight of the reaction mixture to precipitate a reaction product (HPMCAS). The temperature of the reaction mixture just before being mixed with the water of 25° C. was 19.3° C.

The precipitate was washed sufficiently with water and then dried. The dried product was sieved through with a sieve having openings of 2860 μm (#7.5) to obtain HPMCAS powder having a degree of substitution (DS) of acetyl groups of 0.57 (9.6% by weight) and a molar substitution (MS) of succinyl groups of 0.31 (12.2% by weight). The powder had an average L/D ratio of 2.44, wherein L and D mean maximum and minimum diameters of each particle.

The undissolved residue after the HPMCAS powder was dissolved in acetone was analyzed by the following method. After 20 g of acetone was weighed in a 50-mL beaker, it was stirred with a stirring blade in a temperature-controlled bath of 20° C. at a rate of about 200 rpm. The HPMCAS powder (2 g) was added thereto, and one minute after the addition, the stirring blade was stopped to prepare the sample solution to be measured. The sample solution was filtered through a 42-mesh filter. After dried at 80° C. for twenty four hours, the weight of the undissolved residue on the filter was measured.

As a result, the amount of the undissolved residue in a solution of 2 g of the HPMCAS powder in 20 g of acetone was 5.6 mg and the proportion of an undissolved residue at 20° C. determined by the following equation was 0.28% by weight.

Proportion of undissolved residue (%)=(weight of dried aggregated lump/weight of sample)×100

The undissolved residue after the HPMCAS powder was dissolved in an aqueous ammonia solution was analyzed by the following method. The HPMCAS powder (26.6 g) was added to 238 g of purified water and stirred at 300 rpm in a temperature-controlled bath of 20° C. to disperse the powder in the water. The resulting dispersion was subjected to addition of 10% by weight aqueous ammonia solution (3.16 g) necessary for neutralizing the carboxyl group of the HPMCAS, and thirty minutes or sixty minutes after the addition, stirring was terminated, followed by filtration through a 42-mesh filter. After dried for 24 hours at 80° C., the weight of the undissolved residue on the filter was measured to determine a proportion of an undissolved residue at 20° C. of the HPMCAS powder dissolved in the aqueous ammonia solution.

The undissolved residue after the HPMCAS powder was dissolved in a mixed solution of water and an alcohol was analyzed by the following method. The HPMCAS powder (24.5 g) were added to 220.5 g of a mixed solution of water and ethanol having a weight ratio of the water to the ethanol of 2:8, and stirred at a rate of 300 rpm to disperse the power in the solution. A proportion of an undissolved residue at 20° C. in the mixed solution was determined in the same manner as the determination of the proportion of the undissolved residue of the HPMCAS powder dissolved in acetone.

The results of Synthesis Example 1 are shown in Tables 1 and 2.

Synthesis Example 2

HPMCAS powder having a degree of substitution (DS) of acetyl groups of 0.57 (9.6% by weight) and a molar substitution (MS) of succinyl groups of 0.31 (12.2% by weight) were obtained in the same manner as in Synthesis Example 1 except that the reaction mixture was subjected to addition of such an amount of water as to make the viscosity of the reaction mixture become 179.2 Pa·s. The temperature of the reaction mixture just before being mixed with water of 25° C. was 10.0° C.

The HPMCAS powder thus obtained had an average L/D ratio of 2.54, wherein L and D mean maximum and minimum diameters of each particle, respectively. A proportion of an undissolved residue at 20° C. of the HPMCAS powder dissolved in acetone or an aqueous ammonia solution was determined in the same manner as in Synthesis Example 1.

The results of Synthesis Example 2 are shown in Tables 1 and 2.

TABLE 1

| | amounts used | | | | viscosity | temperature |
| --- | --- | --- | --- | --- | --- | --- |
| | glacial acetic acid (g) | succinic anhydride (g) | acetic anhydride (g) | sodium acetate (g) | of reaction mixture (Pa · s) | of reaction mixture (° C.) |
| Syn. Ex. 1 | 960 | 122 | 340 | 290 | 150 | 19.3 |
| Syn. Ex. 2 | 960 | 122 | 340 | 290 | 179 | 10.0 |

TABLE 2

| | L/D of dried product | specific surface area (m²/g) | loose bulk density (g/mL) | portion of undissolved residue in acetone (wt %) | portion of undissolved residue in ammonia water | | portion of undissolved residue in mixed solution of water and ethanol | |
|---|---|---|---|---|---|---|---|---|
| | | | | | 30 mins after addition (wt %) | 60 mins after addition (wt %) | 30 mins after addition (wt %) | 60 mins After Addition (wt %) |
| Syn. Ex. 1 | 2.44 | 3.65 | 0.144 | 0.28 | 0.08 | 0.01 | 0.06 | 0.01 |
| Syn. Ex. 2 | 2.54 | 3.72 | 0.132 | 0.22 | 0.74 | 0.09 | 0.08 | 0.05 |

Reduction of the proportion of the undissolved residue in each solution analyzed in Synthesis Examples 1 and 2 was remarkable, compared with conventional results. According to the conventional results, the proportion of an undissolved residue was from 45 to 55% by weight in an acetone solution, and 1.0 to 1.5% by weight at 30 minutes after each addition of an aqueous ammonia solution and a water-ethanol mixed solution. In Synthesis Examples 1 and 2, in particular, the proportion of the undissolved residue in the acetone solution was small and the powder exhibited excellent solubility.

Example 1

(Production of Tablet)

The HPMCAS powder (100 g) produced in Synthesis Example 1 was dispersed in 1428 g of purified water while stirring with a propeller type stirrer, subjected to addition of 19 g of a 10% by weight aqueous ammonia solution, and the resulting mixture was stirred for 30 minutes. No dissolved substance was observed and a transparent aqueous solution was obtained rapidly.

The resulting aqueous solution was subjected to addition of 10 g of triethyl citrate (i.e. 10 parts by weight relative to 100 parts by weight of HPMCAS) and 30 g of talc (Crown Talc, product of Matsumura Sangyo) (i.e. 30 parts by weight relative to 100 parts by weight of HPMCAS), and the resulting mixture was stirred for 10 minutes to produce a coating composition having a HPMCAS concentration of 7% by weight.

A mixture of 2 parts by weight of Riboflavin (product of Tokyo Tanabe Co., Ltd.), 90 parts by weight of lactose ("Dilactose S", product of Freund Corporation), 8 parts by weight of low-substituted hydroxypropyl cellulose (degree of hydroxypropyl substitution: 11% by weight) and 0.5 part by weight of magnesium stearate was tableted into uncoated tablets each having a weight of 200 mg by a rotary tablet press ("Virgo", product of Kikusui Seisakusho) under the conditions: a tablet diameter of 8 mm, a tableting pressure of 1 t, a pre-tableting pressure of 0.3 t and a rotating speed of 20 rpm.

Each of the uncoated tablets was coated with the coating composition produced above until the weight of the solid portion coated became 7 parts by weight relative to 100 parts by weight of each of the uncoated tablets under the conditions below. Neither clogging of a filter as the coating composition was filtered nor clogging of a spray nozzle was observed.

Apparatus: perforated pan coater (inner diameter: 33 cm)
Amount charged: 1 kg
Air intake temperature: 80° C.
Exhaust air temperature: 42° C.
Air intake rate: 1 m³/min
Rotating speed of pan: 24 rpm
Spray rate: 6 g/min
Spray air pressure: 150 kPa A disintegration test of 20 coated tablets thus obtained was carried out in accordance with the Japanese Pharmacopoeia Sixteenth Edition by using 900 mL of the 1st fluid (pH 1.2) for the Disintegration Test described therein. The 1st fluid corresponding to an artificial gastric fluid is used for evaluating acid resistance, more specifically, resistance against the gastric fluid. The acid resistance was analyzed by measuring a tablet deficit ratio two hours after the disintegration test, as well as the 1st fluid immersion ratio based on the weights of the tablet before and after the test. A tablet having a tablet deficit ratio of 0% and a 1st fluid immersion ratio of 5% or less is defined as the tablet having sufficient acid resistance. As a result, no tablet deficit such as broken film or swollen tablet was observed and thus the tablet had sufficient acid resistance. Next, a disintegration test was carried out in accordance with the Japanese Pharmacopoeia Sixteenth Edition by using 900 mL of the 2nd fluid (pH: 6.8) for the Disintegration Test specified therein. The 2nd fluid corresponding to an artificial intestinal fluid is used for evaluating solubility in an intestinal fluid. As a result of the disintegration test, it was found that the powder was dissolved rapidly in the fluid.

Example 2

(Production of Tablet)

The HPMCAS powder (100 g) produced in Synthesis Example 1 was dispersed in 1328 g of a mixed solution of ethanol and purified water having a weight ratio of the ethanol to the purified water of 8:2 while stirring with a propeller type stirrer for 30 minutes, to obtain a coating solution having a HPMCAS concentration of 7% by weight. No undissolved material was observed and a transparent aqueous solution was obtained rapidly.

A mixture of 2 parts by weight of Riboflavin (product of Tokyo Tanabe Co., Ltd.), 90 parts by weight of lactose ("Dilactose 5", product of Freund Corporation), 8 parts by weight of low-substituted hydroxypropyl cellulose (degree of substitution (DS) of hydroxypropy groups of 0.26 (11% by weight)) and 0.5 part by weight of magnesium stearate was tableted into uncoated tablets each having a weight of 200 mg by a rotary tablet press ("Virgo", product of Kikusui Seisakusho) under the conditions: a tablet diameter of 8 mm, a tableting pressure of 1 t, a pre-tableting pressure of 0.3 t, and a rotating speed of 20 rpm.

Each of the uncoated tablets was coated with the coating solution produced above until the weight of the solid content coated became 7 parts by weight relative to 100 parts by weight of each of the uncoated tablets under the conditions below. Neither clogging of a filter as the coating solution was filtered nor clogging of a spray nozzle was observed.

Apparatus: perforated pan coater (inner diameter: 33 cm)
Amount charged: 1 kg
Air intake temperature: 60° C.
Exhaust air temperature: 35° C.
Air intake rate: 1 m$^3$/min
Rotating speed of pan: 24 rpm
Spray rate: 15 g/min
Spray air pressure: 150 kPa The obtained 20 coated tablets were evaluated in the same manner as in Example 1. As a result, no tablet deficit such as broken film or swollen tablet was observed and thus the tablet had sufficient acid resistance. Next, a disintegration test was carried out in accordance with the Japanese Pharmacopoeia Sixteenth Edition by using 900 mL of the 2nd fluid (pH: 6.8) for the Disintegration Test specified therein. As a result of the disintegration test, it was found that the powder was dissolved rapidly in the fluid.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

That which is claimed is:

1. A method for producing a coating composition, the method comprising dissolving a hypromellose acetate succinate powder having an average ratio of L to D of from 2.0 to 3.0 in a solvent which is a mixed solution of water and an alcohol, or an aqueous ammonia solution,
wherein L and D mean maximum and minimum diameters, respectively, of each particle in the hypromellose acetate succinate powder.

2. The method for producing a coating composition according to claim 1, wherein the hypromellose acetate succinate powder has a specific surface area of from 2.0 to 5.0 m$^2$/g or more.

3. The method for producing a coating composition according to claim 1, wherein the hypromellose acetate succinate powder has a loose bulk density of from 0.10 to 0.25 g/mL.

4. The method for producing a coating composition according to claim 1, wherein the hypromellose acetate succinate powder comprises 10% by weight or less of component not soluble at 20° C. in such a weight of acetone as to be 10 times the weight of the powder.

5. A method for producing a drug-containing particle, comprising:
each step comprised by the method as claimed in claim 1 to obtain a coating composition; and
a step of coating a drug-containing core with the coating composition to form a coat portion over the core.

6. A method for producing a solid preparation, comprising:
the steps comprised by the method as claimed in claim 5 to obtain a drug-containing particle; and
a step of formulating the drug-containing particle into a preparation.

7. The method for producing a solid preparation according to claim 6, wherein the solid preparation is a tablet, a granule or a fine granule.

* * * * *

UNITED STATES PATENT AND TRADEMARK OFFICE
CERTIFICATE OF CORRECTION

PATENT NO. : 11,396,558 B2
APPLICATION NO. : 17/066543
DATED : July 26, 2022
INVENTOR(S) : Matsubara et al.

It is certified that error appears in the above-identified patent and that said Letters Patent is hereby corrected as shown below:

On the Title Page

(54) Title: Please delete the title and replace with the following: HYPROMELLOSE ACETATE SUCCINATE POWDER EXCELLENT IN DISSOLVED STATE AND PRODUCTION METHOD THEREOF, AND PRODUCTION METHODS FOR COMPOSITION FOR SOLID DISPERSION, COATING COMPOSITION, DRUG-CONTAINING PARTICLE, AND SOLID PREPARATION In the Specification Column 1, Title: Please delete the title and replace with the following: HYPROMELLOSE ACETATE SUCCINATE POWDER EXCELLENT IN DISSOLVED STATE AND PRODUCTION METHOD THEREOF, AND PRODUCTION METHODS FOR COMPOSITION FOR SOLID DISPERSION, COATING COMPOSITION, DRUG-CONTAINING PARTICLE, AND SOLID PREPARATION Column 2, Line 52: Please correct "LID" to read --L/D--

Column 2, Line 54: Please correct "LID" to read --L/D--

Column 4, Line 39: Please correct "HS" to read --JIS--

Signed and Sealed this
Eighteenth Day of July, 2023

Katherine Kelly Vidal
*Director of the United States Patent and Trademark Office*